United States Patent
De Castro et al.

[19]

[11] Patent Number: 5,834,626
[45] Date of Patent: Nov. 10, 1998

[54] COLORIMETRIC INDICATORS FOR BREATH, AIR, GAS AND VAPOR ANALYSES AND METHOD OF MANUFACTURE

[76] Inventors: Emory S. De Castro, 60 Little Nahant Rd., Nahant, Mass. 01908-0128;
Douglas R. Malat, P.O. Box 638, Hampton Bays, N.Y. 11946

[21] Appl. No.: 758,557

[22] Filed: Nov. 29, 1996

[51] Int. Cl.⁶ .............................. G01N 27/62; G01N 1/22
[52] U.S. Cl. .................... 73/23.3; 73/29.01; 73/31.03; 73/25.04; 422/83; 422/85; 422/86
[58] Field of Search .................. 73/23.3, 23.34, 73/31.02, 31.03, 25.04, 29.01; 422/84, 85, 86, 83

[56] References Cited

U.S. PATENT DOCUMENTS

| Re. 27,008 | 12/1970 | Luckey | 23/254 |
|---|---|---|---|
| Re. 31,914 | 6/1985 | Oswin et al. | 204/1 |
| Re. 31,915 | 6/1985 | Oswin et al. | 204/195 R |

(List continued on next page.)

FOREIGN PATENT DOCUMENTS

| 1143818 | 2/1969 | Br. Indian Ocean Ter. . |
| 133326 A2 | 2/1985 | European Pat. Off. . |
| 577263 A1 | 1/1994 | European Pat. Off. . |

*Primary Examiner*—Hezron E. Williams
*Assistant Examiner*—J. David Wiggins
*Attorney, Agent, or Firm*—Alfred M. Walker; Harvey Lunenfeld

[57] ABSTRACT

Colorimetric indicators for breath, air, gas, & vapor analyses that can be thrown away after a single use, are easy to use, low cost, small, and simple to manufacture for indicating at least volume passed through the colorimetric indicators and may also be used to indicate concentration of an analyte within breath, air, gas, & vapor passed through the colorimetric indicators. The present invention is directed to colorimetric indicators for breath, air, gas, & vapor analyses. The colorimetric indicators may have a housing with an entrance port, an outlet, a volume indicator, and an analyte indicating reagent. The volume indicator may be a breath volume reagent. Different analytes may be measured, the analyte indicating reagent depending upon the particular analyte being to monitored. The breath volume indicator is colorimetric, and changes color when a predetermined volume of air is passed through the colorimetric indicators for breath, air, gas, & vapor analyses. The analyte indicator reagent is also colorimetric, and changes color when a predetermined amount of chemical concentration of the analyte is exposed to the analyte indicator reagent. A process for manufacturing a colorimetric indicator for breath, air, gas, and vapor analyses, comprises at least the following steps: immobilizing a reagent, such color change inducing reagent being composed of at least one constant concentration component.

42 Claims, 6 Drawing Sheets

U.S. PATENT DOCUMENTS

| | | | |
|---|---|---|---|
| 3,388,975 | 6/1968 | Wallace | 23/254 |
| 3,437,449 | 4/1969 | Luckey | 23/254 |
| 3,647,391 | 3/1972 | Keyes | 23/254 |
| 3,676,073 | 7/1972 | Luckey | 23/232 |
| 3,772,909 | 11/1973 | Anderson | 73/23.1 |
| 3,792,272 | 2/1974 | Harte | 250/343 |
| 3,888,628 | 6/1975 | Graham | 23/230 |
| 3,916,534 | 11/1975 | Riccio | 35/11 |
| 3,925,183 | 12/1975 | Oswin et al. | 204/195 |
| 3,998,591 | 12/1976 | Eckfeldt | 23/253 R |
| 4,093,945 | 6/1978 | Collier et al. | 340/279 |
| 4,140,106 | 2/1979 | Kirmaier | 128/2 |
| 4,161,875 | 7/1979 | Stuitje | 73/23 |
| 4,277,251 | 7/1981 | Leichnitz | 23/232 R |
| 4,294,583 | 10/1981 | Leichnitz | 23/232 |
| 4,297,871 | 11/1981 | Wright et al. | 73/23 |
| 4,329,318 | 5/1982 | Le Grouyellec et al. | 422/59 |
| 4,421,719 | 12/1983 | Burleigh | 422/57 |
| 4,492,673 | 1/1985 | Eriksen et al. | 422/85 |
| 4,642,286 | 2/1987 | Moldowan | 435/25 |
| 4,740,475 | 4/1988 | Paul | 436/165 |
| 4,749,553 | 6/1988 | Lopez et al. | |
| 4,791,065 | 12/1988 | Rislove | 436/132 |
| 4,810,633 | 3/1989 | Bauer et al. | 435/25 |
| 4,826,774 | 5/1989 | Nagel | 436/106 |
| 4,828,800 | 5/1989 | Castleman | 422/83 |
| 4,839,296 | 6/1989 | Kennedy et al. | 436/170 |
| 4,863,694 | 9/1989 | Kimmel et al. | 422/86 |
| 4,905,498 | 3/1990 | O'Donnell et al. | 73/23.1 |
| 4,933,144 | 6/1990 | May | 422/60 |
| 4,962,025 | 10/1990 | Moldowan | 435/25 |
| 4,994,238 | 2/1991 | Daffern et al. | 422/56 |
| 5,032,506 | 7/1991 | Palmer et al. | 435/26 |
| 5,055,268 | 10/1991 | Martin | 422/84 |
| 5,059,790 | 10/1991 | Klainer et al. | 250/227.21 |
| 5,089,232 | 2/1992 | May | 422/83 |
| 5,171,535 | 12/1992 | Lamont | 422/85 |
| 5,174,959 | 12/1992 | Kundu et al. | 422/59 |
| 5,185,247 | 2/1993 | Ismail et al. | 435/14 |
| 5,196,302 | 3/1993 | Kidwell | 435/4 |
| 5,220,919 | 6/1993 | Phillips et al. | 128/632 |
| 5,274,550 | 12/1993 | Greenlee | 364/413.09 |
| 5,291,887 | 3/1994 | Stanley et al. | 128/637 |
| 5,309,921 | 5/1994 | Kisner et al. | 128/719 |
| 5,328,664 | 7/1994 | Ponsy | 422/84 |
| 5,334,502 | 8/1994 | Sangha | 435/7.21 |
| 5,369,977 | 12/1994 | Rhodes et al. | 73/23.3 |
| 5,403,749 | 4/1995 | Khartchenko | 436/132 |
| 5,417,204 | 5/1995 | Moesle, Jr. | 128/205.23 |
| 5,426,415 | 6/1995 | Prachar et al. | 340/576 |
| 5,429,931 | 7/1995 | Detwiler et al. | 435/26 |
| 5,439,648 | 8/1995 | Balderson et al. | 422/86 |
| 5,445,795 | 8/1995 | Lancaster et al. | 422/86 |
| 5,454,375 | 10/1995 | Rothenberg | 128/716 |
| 5,472,668 | 12/1995 | Mills et al. | 422/56 |
| 5,501,231 | 3/1996 | Kaish | 128/725 |

*Fig. 4A*
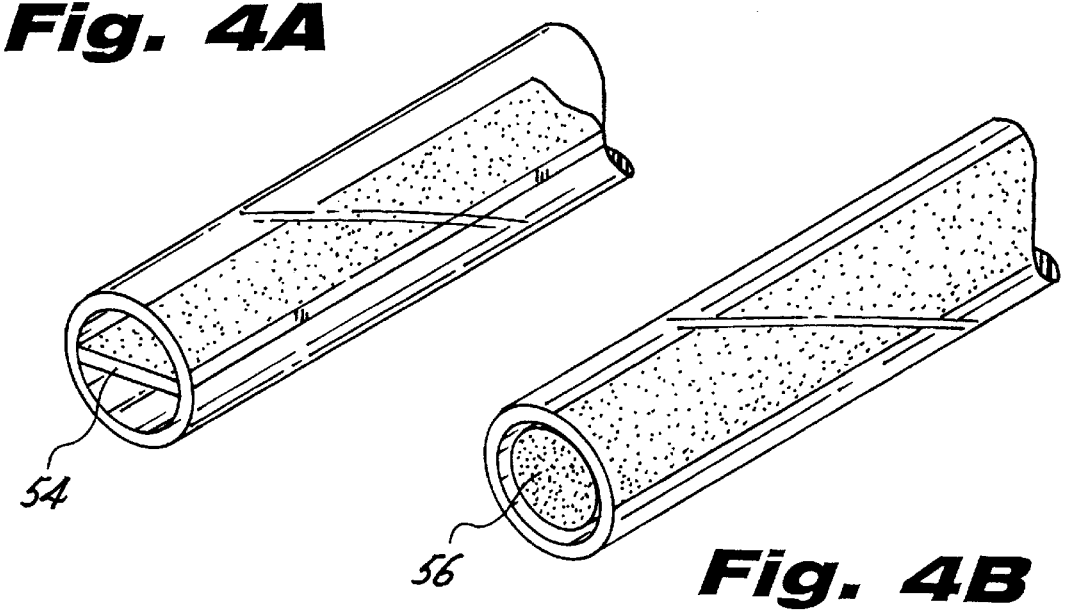
*Fig. 4B*
*Fig. 5A*
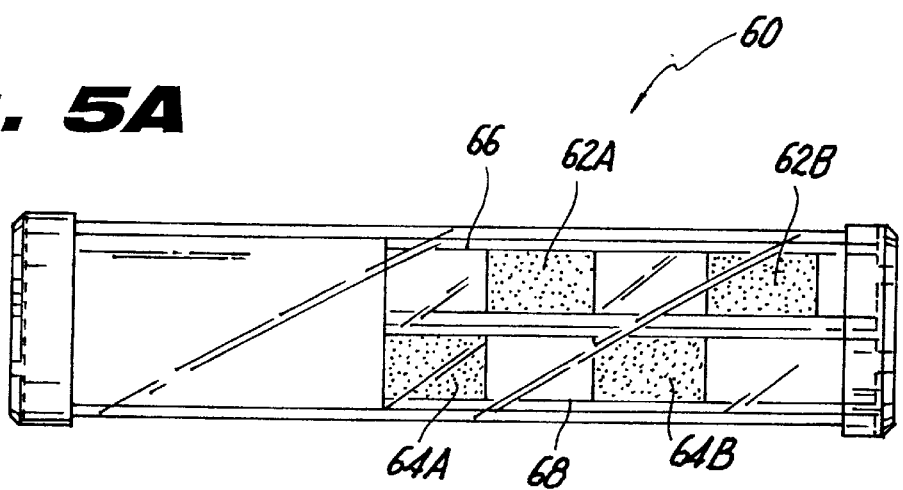
*Fig. 5B*
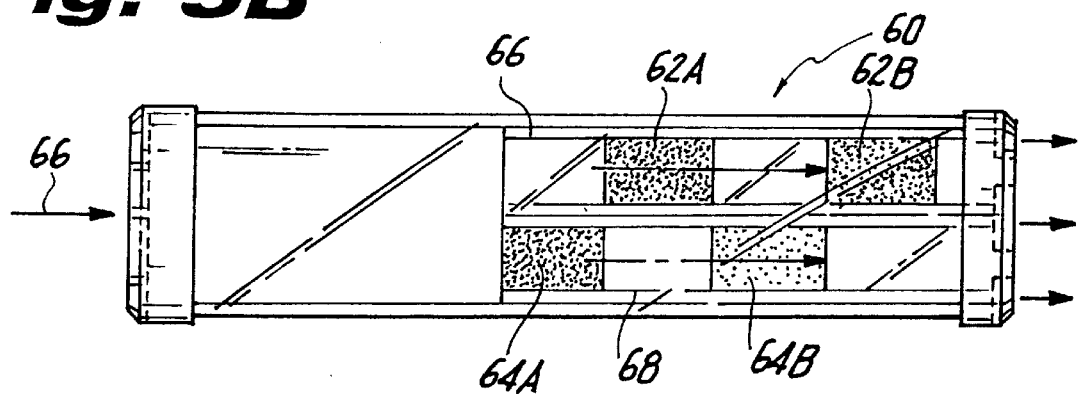

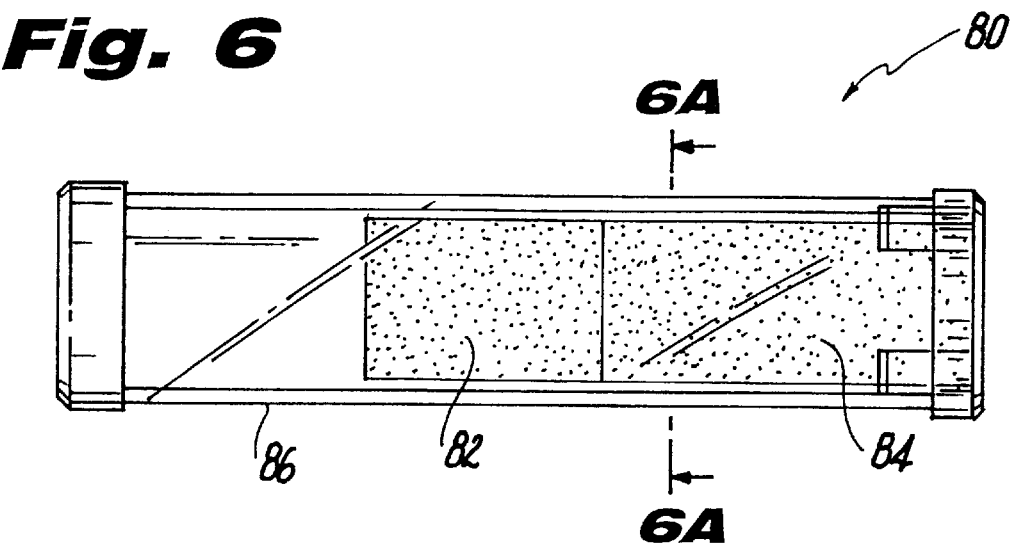
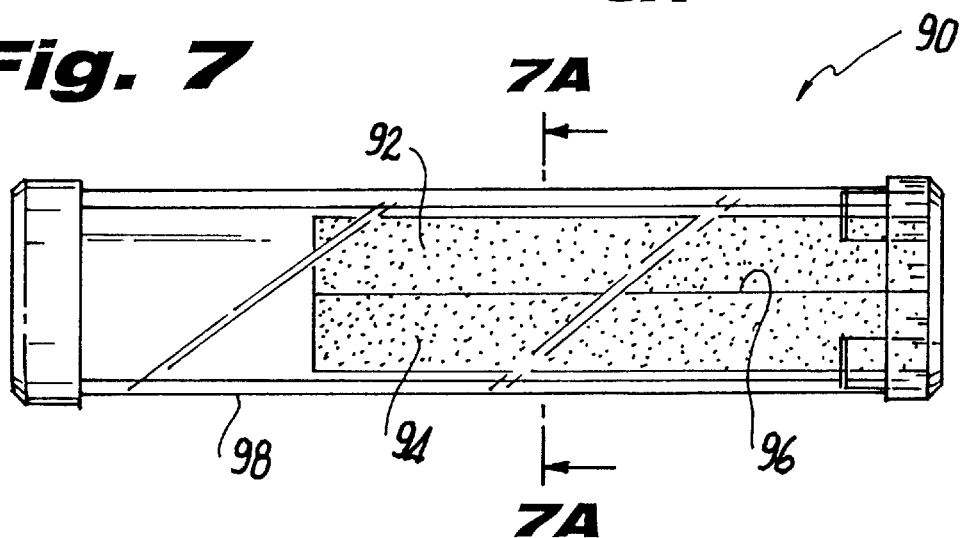
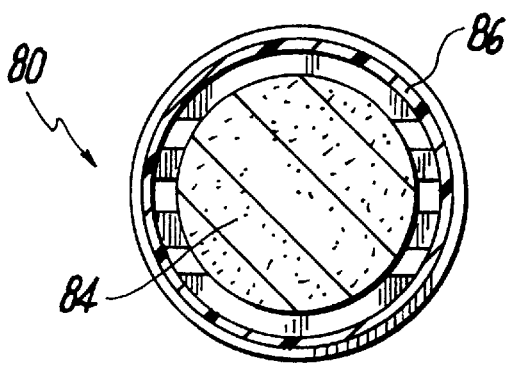
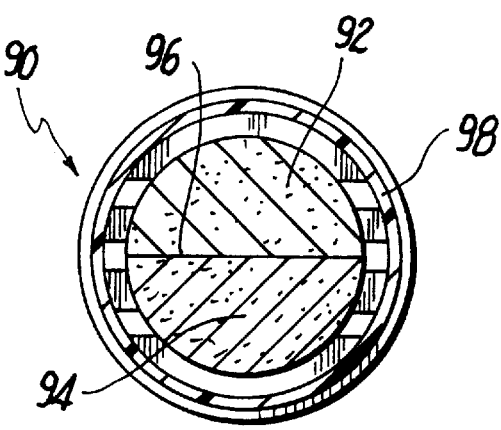

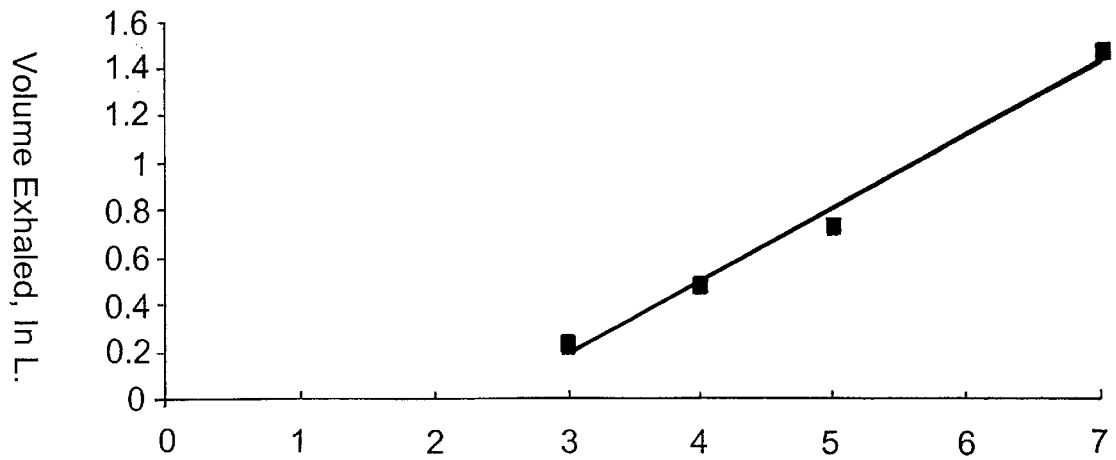
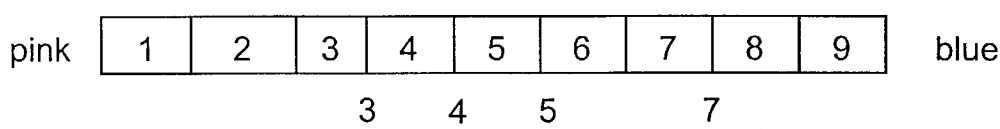
Transition zone of change from pink to blue
Exhaled breath volume vs. segment of multi-segmented strip
Fig. 10
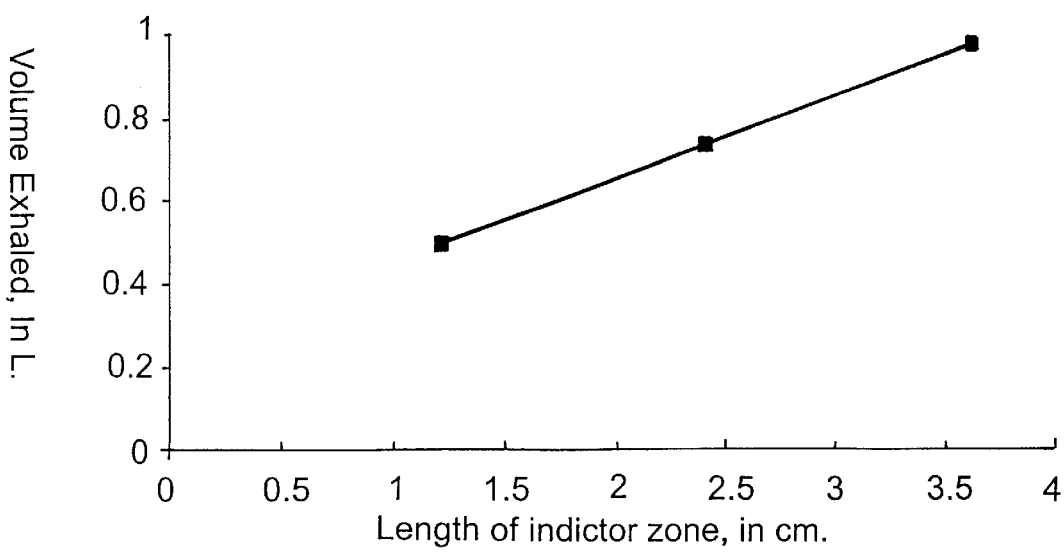
Exhaled breath volume vs. length of indicator
Fig. 11

COLORIMETRIC INDICATORS FOR BREATH, AIR, GAS AND VAPOR ANALYSES AND METHOD OF MANUFACTURE

BACKGROUND OF THE INVENTION

1. Field of the Invention

The present invention relates generally to indicators for breath, air, gas, & vapor analyses, and more particularly to colorimetric volume and gas indicators.

2. Background

Methods for quantitative analysis of chemicals and concentrations of chemicals in breath, air, gas, and vapors generally require knowledge of a quantity of such chemicals in a volume under consideration. Chemical concentration may be quantified by measuring the quantity of such chemicals in a volume of breath, air, gas, and/or vapors. The concentration may be determined by measuring the amount of such chemicals and the volume of breath, gas, and/or vapors containing the chemicals, or alternatively, by having a prior knowledge of either or both the amount of such chemicals and/or the volume.

Devices for the measurement of chemical concentrations in breath, air, gas, and/or vapors have heretofore been known. However, inexpensive, small, throwaway devices that are capable of measuring such chemical concentrations that may be discarded after a single use have not been available.

Applications for such devices, for example, include breath analyzers which may be used for measuring alcohol content in a human being's breath. Moreover, as a result of viruses, bacteria, and contagious pathogens commonly associated with human breath, it is highly desirable to measure alcohol content in a human's breath, using a small portable, inexpensive, throwaway device, which provides the advantage of not contaminating a future user or recontaminating a user, during or after a second or repeated use. There is thus a need for a device that may be thrown away after first use, a new and unused device being used for each subsequent measurement. Use of such a throwaway, small, portable, inexpensive device has far reaching implications, well beyond application to measurement of alcohol content in a human's breath and may be used in a variety of chemical, pharmaceutical, and biological processes and applications.

User' lung capacities vary greatly, depending on body mass and cardiovascular health. Thus, means for accurately controlling or indicating volume breathed into or passed through a measuring device is critical for an accurate indication of alcohol in a user's breath.

Electrochemical methods for alcohol measurement in a user's breath have heretofore been known. These methods generally depend upon a user breathing into a device, such as a mouth piece connected to an inflatable balloon, wherein the device converts alcohol concentration in the user's breath into an electrical signal, using an electrochemical cell.

Various electrochemical cells have been known. One such electrochemical cell uses ethanol as a fuel in the electrochemical cell, such that oxygen is reduced and ethanol is oxidized. Another device maintains the potential of one electrode of the electrochemical cell constant and measures the current that develops when an oxidizable substance, such as ethanol contacts the electrode. Such electrochemical cells are called "amperometric" cells. The resultant current from both fuel cell and amperometric cells is proportional to not only the concentration of ethanol but also the rate at which the user's breath is exhaled. Thus, for an electrochemical device to work properly, some means must be employed to either fix the volume on flow rate of the breath exhaled by the user. The current is also dependent on the temperature of the electrochemical cell, the type of electrode material employed, and the history of the electrode (for the case of passivating interferences). Acknowledging these shortcomings, inventors have attempted to develop devices and methods to overcome limitations of the electrochemical cells.

U.S. Pat. No. 3,925,183 (Oswin et al), for example, discloses an electrochemical (amperometric) cell in which a reservoir is filled by a user, a valve closes a sampling port of the reservoir, and a separate pump then samples the reservoir at a controlled rate. While fulfilling the need to achieve a controlled rate, the device is complex and expensive, with a pump, valves, and timing circuitry required.

U.S. Pat. No. 5,369,977 (Rhodes et al) describes an electrochemical cell similar to the device described in U.S. Pat. No. 3,925,183 (Oswin et al), using a system of valves and pumps. A pressure valve is used to detest when a user expels a sufficient volume of breath. The device has an on-board pressurized reference sample of ethanol, which is used to alleviate on-going changes in electrode response and performance. While obtaining some notable improvement in performance over U.S. Pat. No. 3,925,183 (Oswin et al), the device described in U.S. Pat. No. 5,369,977 (Rhodes et al) is too expensive and complex to be deplored in disposable, single-use, mass-market throwaway applications.

U.S. Pat. No. 4,093,945 (Collier et al), U.S. Pat. No. 5,426,415 (Prachar et al), and U.S. Pat. No. 5,055,268 (Martin) describe electrochemical cells employing fans, pumps, valves, electronic mass flow meters, and/or some combination of each to achieve a known volume or determination of such volume, using a constant flow rate for introduction of a sample.

U.S. Pat. No. 4,297,871 (Wright et al) discloses a device used to sample exhaled breath, having of a series of channels, springs, chambers, and pressure sensors. In this and the above citations, the cost and complexity of the components, while suitable for law enforcement officials, are not suitable for the occasional social imbiber with the need to know his or her own alcohol level.

Optical devices have also been disclosed. For example, U.S. Pat. No. 3,792,272 (Harte, et al) and U.S. Pat. No. 3,792,272 (Kisner et al) describe optical systems for determining organic components in breath, each being of substantial cost and complexity that do not serve the market for occasional users. A simple test strip that gives a visible color as an indication of inebriation status is more appropriate. Several have offered solutions.

Gas collecting and volume measuring devices have been disclosed. For example, U.S. Pat. No. 5,171,535 (Lamont) describes a breath alcohol tester having an alcohol reactant substance within a tube and a gas-collecting bladder affixed to an end of the tube. A user blows into the tube until the bladder is filled. The user's breath contacts the alcohol reactant substance and is captured in and prevented from exiting the bladder by a one-way valve. The size of the inflated bladder gives the user a relative indication of the volume of breath exhaled. One shortcoming that prevents the device's efficacy is that a user has no idea as to the size that the collection bladder must attain for sampling to be complete. The user can thus blow too little or too much, which in either case results in a false reading. A consumer objection to such a device is having attention called to the user, during the bladder inflation process, thus decreasing appeal of the device to many would-be users. In a social setting, a user would prefer a discrete device that is small, easy to carry in a pocket, and can be quickly used without notice by others.

British Patent No. 1,143,818 (Ducie and Jones) describes a device in which a transparent tube is filled with an alcohol-sensitive reagent immobilized on a bed of silica gel. The user attaches a tube to a bag and blows into the bag via the tube. Once the bag is filled, the user stops blowing into the tube and notes a color change, the length of color change along the silica indicating the degree of alcohol in the user's breath. Without prior knowledge of the degree to which the bag must be filled, however, a user can easily overpressurize or under fill the bag, causing false positive and/or false negative readings on the indicator. Additionally, the user must have sufficient dexterity to securely fit the mouthpiece-tube into the bag, and if the user is inebriated, this operation may be difficult. Further, the necessity of using a bag limits the minimum size of the device and is an impediment to users who will not want to carry this additional bulk.

European Patent Application EP 577263 A1 (filed 1 Jan., 1994) (Liu) describes a device which makes use of a tube and a control piece, wherein color is used to estimate blood alcohol. However, no provisions are employed to control or accurately indicate a volume of air passing through the tube, which is required to accurately indicate alcohol in a user's breath.

Luckey addresses the need for volume measurement in U.S. Pat. No. 3,437,449 (Luckey), which discloses a multi-balloon device. Here, Luckey describes a method to obtain alveolar breath, that is, breath in steady-state equilibrium with a user's blood supply, since alveolar breath would more closely reflect actual blood alcohol levels. The user first fills an inelastic balloon element to a predetermined size. The filled balloon is then coupled to another balloon, and the sampled breath is forced through a color-indicating reagent for alcohol. Once the second balloon is filled, the user halts the transfer. In U.S. Pat. 3,676,073 (Luckey), Luckey also describes applying this multi-balloon device to a tube filled with only silica to trap the alcohol. This non-color changing device is then sent to a lab for analytical measurement of the trapped alcohol. These approaches in Luckey '073 and Luckey '449 add unnecessarily complex measures that an uneducated consumer would find difficult to follow. Also, the approaches in Luckey '073 and Luckey '449 produce a devices hardly amenable to being carried in a shirt-pocket or pocket-book.

European Patent Application 0,133,326 (filed 22 Feb., 1984) (Schmitz) recognizes the need to sample alveolar breath and describes a pocket-sized disposable breath analyzer. Instead of a multitude of balloons, EPO 0,133,326 of Schmitz relies on mechanical switching activated by a certain breath pressure through the device. A plastic shuttle moves across a set of intake holes, thereby changing the path of the exhaled breath through an appropriate region, containing a colorimetric reagent for alcohol. EPO 0,133,326 of Schmitz notes that either the duration of breath can be timed, presumably with a watch, or an optional bag can be attached. Clearly, both these approaches to volume measurement (a watch or a bag) will not be appropriate: the timed method assumes all users breath at the same rate, with the same pressure, and with the same lung capacity. The deficiencies of the bag have been previously described. Also, the additional complexity of finely machining the shuttle and associated pathways adds to the cost of the device.

Devices for analyzing for blood alcohol content in saliva have been disclosed. For example, in U.S. Pat. No. 5,334,502 (Sanghi), Sanghi attempts to analyze for blood alcohol via ethanol content in saliva. In order to use the device of Sanghi '502, a user must first collect his or her saliva, and inject the liquid onto a test strip area. The liquid saliva activates a dye. Once a specified color is obtained, the user stops placing saliva on the device. Next the user waits for the saliva to dry, and then subjects the strip to additional tests for alcohol. Clearly, such sampling and time delays would not be appropriate for a consumer in a social setting. Furthermore, the series of steps a user must take to obtain a result may be too complex for a user suffering from inebriation.

Similarly, U.S. Pat. No. 4,740,475 (Paul) discloses a device for measuring ethanol content in saliva. Here a sealed vial within a tube acts as a pump. Breaking the vial releases a vacuum that then sucks up a known volume of saliva through an ethanol reagent. U.S. Pat. No. 5,032,506 (Palmer et al) also discloses a device for sampling saliva. Capillary action through a small tube controls the volume of saliva sampled for alcohol. U.S. Pat. No. 4,994,238 (Daffern et al) uses a geometric hollow filled device with an absorbent paper to create a constant volume chamber for saliva sampling. However in these and other devices sampling saliva, there is consumer reluctance to handle a user's own body fluids or transfer such body fluids to a sampling device. Again, in both Palmer et al '506 and Daffern '238, some awareness is needed to fill the devices to a specified level. A much more accepted and easier device and/or method would be to merely blow into a tube.

An alternate to electrochemical analyzers is an enzymatic chemical strip placed in contact with blood or saliva. This sophisticated analysis, with proper controls, can determine the amount of alcohol in blood, providing sufficient care is taken in controlling the reaction time. For example, in U.S. Pat. 5,429,931 (Detwiler et al) discloses a method for immobilizing alcohol dehyrogenase and an oxidized nicotinamide coenzyme to determine alcohol in whole blood, serum, or plasma.

A non-enzymatic reagent for the determination of ethanol is disclosed in U.S. Pat. 5,403,753 (Khartchenko et al) and as in Detwiler '931, which requires direct contact of saliva or other body fluids to determine the presence of alcohol. The non-enzymatic approach that requires an incubation period, as well as mixing a measured quantity of saliva may not hold up for consumer use since there is a general aversion among the public to handling bodily fluids as well as a need to know the result in a timely manner. Neither of these approaches use breath analysis, a generally acceptable and convenient approach for alcohol detection.

Electronic devices have been disclosed. For example, a more complex electrochemical device to prevent driving while intoxicated is sold by Alcohol Sensors International Ltd., Ronkonkoma, N.Y. This breathalyzer is computer-actuated and electronically controls the ignition of an automobile. If a driver has imbibed too much alcohol, the vehicle ignition is inhibited. Furthermore, if the device senses too much alcohol in a person already driving, various alarm functions are sounded until the driver pulls over. This device, while effective for the habitual drinker, would not be appropriate for the mass market of occasional imbibers. An electrochemical device in the form of a patch fixed to the skin, which is used with a computer, is described in U.S. Pat. No. 5,220,919 (Philips et al). The patch is computer controlled and incorporates a transmission signal, enabling a remote modem able to poll the status of the subject wearing the device and relay instantaneous blood alcohol levels to surveillance stations.

A predictive device has been disclosed. This patented device is a miniature calculator designed to help drinkers predict their blood-alcohol level, as shown in U.S. Pat. No. 5,274,550. A user inputs his or her sex, height, and weight once, which is stored in a microprocessor. When the user anticipates imbibing an alcoholic beverage, the user inputs the type of beverage that he or she expects to drink i.e., beer, wine, or distilled spirits, into the device. If the calculator indicates that the next drink will put the drinker over a 0.08% blood alcohol level, a red light goes is illuminated. Below 0.05% a green light is illuminated, and between 0.05% and 0.08% a yellow light is illuminated.

All of the above described devices and approaches are either:

1. too expensive for consumer use and use by the general public;
2. procedurally too complex to obtain reasonable results in a real life situation of actual use in the field by the general public;
3. require too long of a time period before obtaining results in a real life situation of actual use in the field by the general public;
4. too cumbersome or absent a method for controlling and/or indicating breath volume; and/or
5. socially unacceptable and awkward to use in public and do not allow for discreet use of the device and/or approach.

Different devices for chemical, gas and volume measuring devices have heretofore been known. However, none of the indicators for breath, air, gas, & vapor adequately satisfies these aforementioned needs.

For the foregoing reasons, there is a need for colorimetric indicators for breath, air, (gas, & vapor analyses that are: inexpensive and that may be used by consumers and by the general public; are procedurally simple and obtain reasonable results in a real life situation of actual use in the field by the general public; require a short time to obtain results in a real life situation of actual use in the field by the general public; are small and have a method for controlling and/or indicating breath volume; and may be used discreetly in social situations and that may be used easily in public.

SUMMARY

The present invention is directed to colorimetric indicators and a method of manufacture for breath, air, gas, & vapor analyses that can be thrown away after a single use, are easy to use, low cost, small, and simple to manufacture.

A colorimetric indicator for breath, air, gas, and vapor analyses having features of the present invention comprises: a housing for containing at least one chemical reactant, having an inlet for passage of the breath, air, gas, and vapor into the housing, an outlet for passage of the breath, air, gas, and vapor out of the housing, a volume within the housing for passage of the breath, air, gas, and vapor through the housing from the inlet to the outlet and for contacting the breath, air, gas, and vapor with the chemical reactant, at least one of the chemical reactants for indicating a quantity of the breath, air, gas, and vapor passed through the colorimetric indicator for breath, air, gas, and vapor analyses.

The colorimetric indicator for breath, air, gas, and vapor analyses may comprise a hand held housing, having an open breathing mouthpiece at one end and an open output port at another end, a breath volume indicator and an analyte indicator reagent. The breath volume indica or may be colorimetric, and change color when a predetermined volume of exhaled breath is breathed into the colorimetric indicator for breath, air, gas, and vapor analyses. The analyte indicator reagent may be used to determine chemical concentration of an analyte, such as alcohol or other chemical, may be colorimetric, and change color, when a predetermined amount of the analyte is exposed to the analyte indicator reagent.

A process for indicating substances in breath, air, gas, and vapor analyses, comprises at least the following steps: contacting at least one chemical reagent with breath, air, vapor, or gas, observing when a predetermined volume of breath, air, gas, or vapor has contacted the chemical reagent; observing state of the chemical reagent when the predetermined volume of breath, air, gas, or vapor has contacted the chemical reagent.

A process for manufacturing a colorimetric indicator for breath, air, gas, and vapor analyses, comprises at least the following steps: immobilizing a reagent, said reagent being composed of at least one constant concentration component.

The process for manufacturing a colorimetric indicator for breath, air, gas, and vapor analyses, may also comprise at least the following steps: applying a predetermined quantity of a chemical accumulator, such as silica gel, onto a support; or in the case of a planar support, onto a predetermined length of a support strip; and employing a combination of amount of accumulator and amount or length of support so that a fixed amount of an unknown quantity, such as volume or the presence of alcohol can be determined without reference to analysis of flow rates.

BRIEF DESCRIPTION OF THE DRAWINGS

These and other features, aspects, and advantages of the present invention will become better understood with regard to the following description, appended claims, and accompanying drawings where:

FIG. 3C is a section view of the volume indicator and the analyte indicator conduit of FIGS. 3A and 3B housed within an outer tube and showing an end cap with entrance ports for exhaled breath, wherein FIG. 3C is taken along line 3C—3C of FIG. 3A;

FIG. 4A is a perspective close-up view in partial section of a second alternate embodiment for a colorimetric indicator for breath, air, gas and vapor analyses, wherein a single conduit is bisected by a separator member;

FIG. 4B is a perspective close-up view in partial section of a third alternate embodiment for a colorimetric indicator for breath, air, gas and vapor analyses, wherein a single conduit encloses a another conduit coaxially;

FIG. 5A is an overall view of a fourth alternate embodiment for a colorimetric indicator for breath, air, gas and vapor analyses, wherein one segmented conduit indicates volume of breath and the other segmented conduit indicates the presence of various concentrations of analytes, before reaction with exhaled breath;

FIG. 5B is an overall view of the colorimetric indicator for breath, air, gas and vapor analyses as shown in FIG. 5A, wherein one segmented conduit indicates volume of breath and the other segmented conduit indicates the presence of various concentrations of analytes, after reaction with exhaled breath;

FIG. 6 is a representation of a fifth alternate embodiment for a colorimetric indicator for breath, air, gas and vapor analyses, in which one zone indicates breath volume and another zone indicates presence of a specific analyte, before reaction with exhaled breath;

FIG. 6a is a cross sectional view of the colorimetric indicator as in FIG. 6, taken along line 6a—6a therein.

FIG. 7 is a sixth alternate representation of a single conduit colorimetric indicator for breath, air, gas and vapor analyses device constructed in accordance with the present invention, in which one zone indicates breath volume and another zone indicates presence of a specific analyte, the zones being parallel, before reaction with exhaled breath.

FIG. 7a is a cross sectional view of the colorimetric indicator as in FIG. 7, taken along line 7a—7a therein.

FIG. 10 is a diagram chart of data from a transition zone of the sixth alternate embodiment for a colorimetric indicator for breath, air, gas and vapor analyses of the present invention as in FIGS. 5A and 5B, showing exhaled breath volume vs. a segment of the multi-segmented strip therein; and, FIG. 11 is a diagram chart of data from a colorimetric indicator for breath, air, gas and vapor analyses of the present invention as in FIG. 4A, showing exhaled breath volume vs. length of the indicator therein.

DESCRIPTION

Detailed Description of the Embodiments

The preferred embodiments of the present invention will be described with reference to FIGS. 1–11 of the drawings. Identical elements in the various figures are identified with the same reference numbers.

Figure 1:
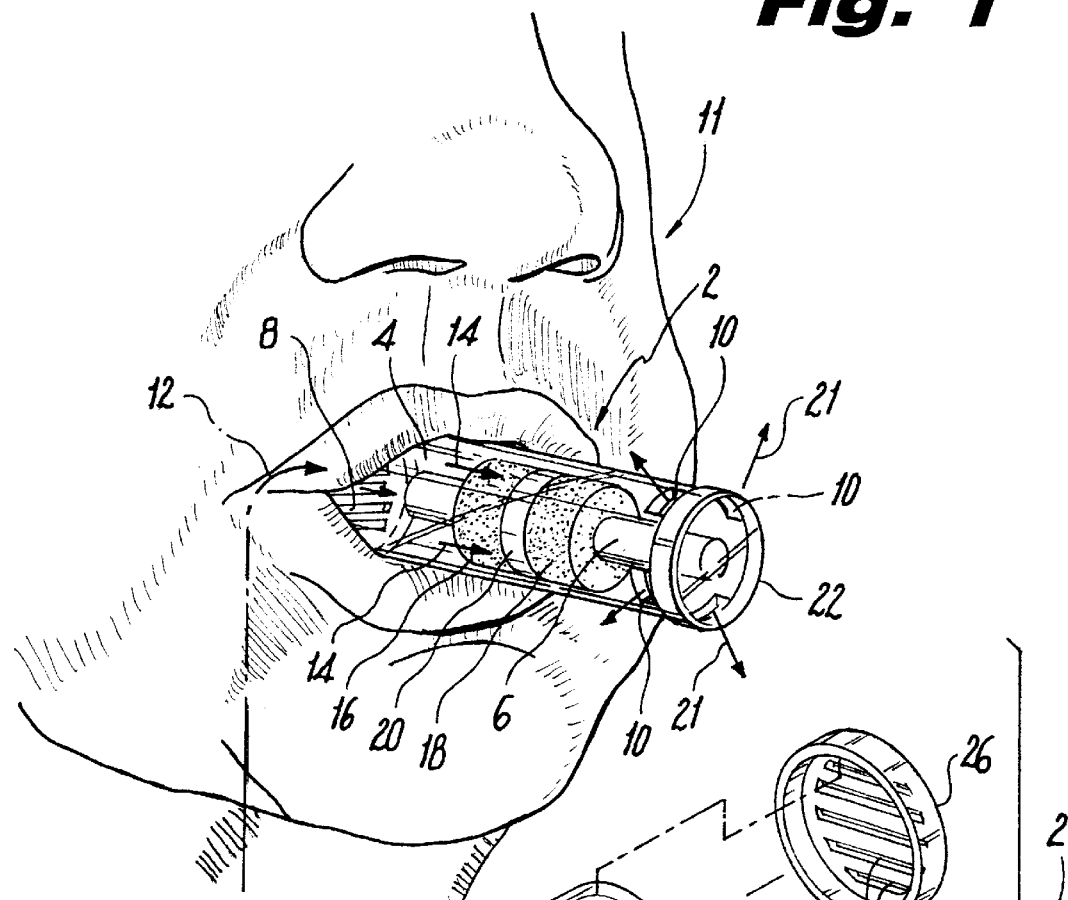
FIG. 1 is a perspective view of an embodiment for a colorimetric indicator for breath, air, gas and vapor analyses, in accordance with the present invention, shown in use.

FIG. 1 shows an embodiment of the present invention, a colorimetric indicator for breath, air, gas, & vapor analyses 2 with an outer tube 4, a coaxially located inner rod 6, at least one entrance port 8, and at Least one exit port 10. A user 11 breathes into the colorimetric indicator for breath, air, gas, & vapor analyses 2, and exhaled breath 12 from the user 11 enters the entrance ports 8. Upon entering the colorimetric indicator for breath, air, gas, & vapor analyses 2, the exhaled breath 12 flows coaxially between the inner rod 6 and the outer tube 4, along paths 14, and then contacts breath volume indicators 16 and 18, and coaxial analyte indicator reagent 20, also located coaxially between the outer tube 4 and the inner rod 6. After contacting the breath volume indicators 16 and 18, and the coaxial analyte indicator reagent 20, the exhaled breath 12 exits the colorimetric indicator for breath, air, gas, & vapor analyses 2 through the exit ports 10 along discharge paths 21. The coaxial breath volume indicators 16 and 18 and the coaxial analyte indicator reagent 20 have sufficient porosity such that the exhaled breath 12 of the user 11 is easily blown through and around the circumferential periphery of the coaxial breath volume indicators 16 and 18 and the coaxial analyte indicator reagent 20 without undue strain on the part of the user 11.

The user 11 blows into the colorimetric indicator for breath, air, gas, & vapor analyses 2 until the coaxial breath volume indicators 16 and 18 each change color. The user 11 stops blowing into the colorimetric indicator for breath, air, gas, & vapor analyses 2, when the coaxial breath volume indicators 16 and 18 each change to the same color. Once the coaxial breath volume indicators 16 and 18 have changed to the same color, a fixed volume of exhaled breath 12 will have passed through the colorimetric indicator for breath, air, gas, & vapor analyses 2, and the user 11 stops blowing into the entrance port 8. The user 11 observes the color of the coaxial analyte indicator reagent 20. At that time, the coaxial analyte indicator reagent 20 will have been subjected to complete contact with the user's exhaled breath 12. If the exhaled breath 12 contains a concentration of analyte above a predetermined threshold concentration, then the analyte indicator reagent 20 will change to a contrasting color and indicate that the user 11 has exceeded such threshold limitations for analyte containing vapors. If the coaxial analyte indicator reagent 20 changes color, then the alcohol content of the exhaled breath 12 of the user 11 is above a preset threshold level. If the coaxial analyte indicator reagent 20 does not change color, then the exhaled breath 12 of the user 11 is below the preset threshold level. The preset threshold level can be based upon a state or country's regulatory and legal standards, for example, for driving a motor vehicle while inebriated or being impaired and under the influence of alcohol.

Under actual environmental conditions, for example, the user 11 could perform a test using the colorimetric indicator for breath, air, gas, & vapor analyses 2, prior to driving a motor vehicle, in order to determine whether the user 11 would be considered fit to drive the motor vehicle, in accordance with the state or country's regulatory and legal standards for alcohol. If the preset threshold is exceeded, then it is recommended that the user 11 not drive the motor vehicle.

Figure 2:
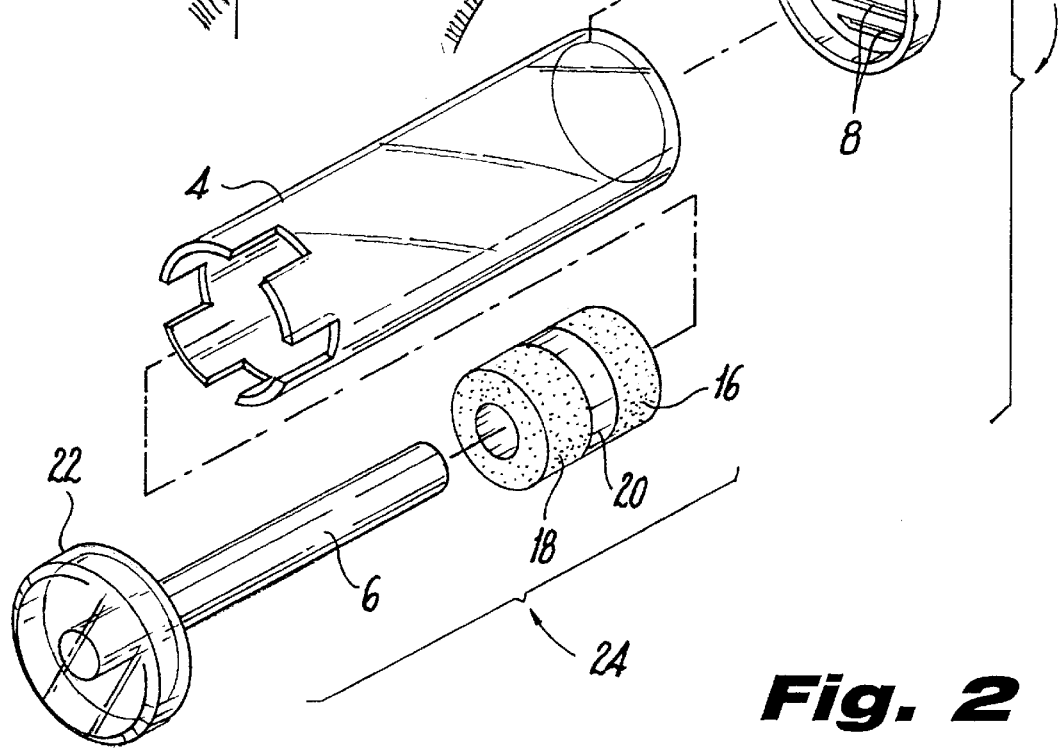
FIG. 2 is an exploded perspective view of the colorimetric indicator for breath, air, gas and vapor analyses, as in FIG. 1.

FIG. 2 shows an exploded perspective view of the present invention, the colorimetric indicator for breath, air, gas, & vapor analyses 2 shown in FIG. 1. The colorimetric indicator for breath, air, gas & vapor analyses 2 may be constructed of transparent polyvinyl chloride material, glass, or other suitable material that allows the user 11 to observe the breath volume indicators 16 and 18 and the coaxial analyte indicator reagent 20 each change color. The inner rod 6 may be sonically welded or affixed by other suitable means coaxially to exit end cap 22. The breath volume indicators 16 and 18 and the coaxial analyte indicator reagent 20 are then slid over the inner rod 6, and assembly 24 of the inner rod 6, the breath volume indicators 16 and 18 and the coaxial analyte indicator reagent 20, which is adjoined to the exit end cap 22, are then inserted into the outer tube 4. The exit ports 10 are formed upon inserting the assembly 24 into the outer tube 4 and abutting the exit end cap 22 coaxially with the outer tube 4. The exit end cap 22 of the assembly 24 may be sonically welded or affixed by other suitable means coaxially to the outer tube 4. Entrance port end cap 26 may be sonically welded or affixed by other suitable means coaxially to the outer tube 4 at an opposing end of the outer tube 4, either before or after affixing the exit end cap 22 to the outer tube 4.

Figure 3A:
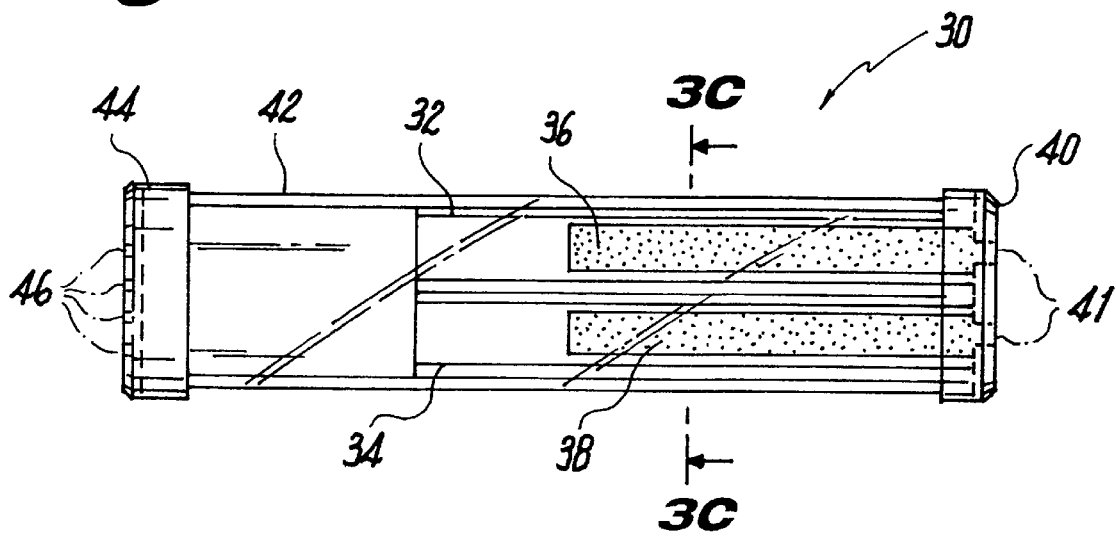
FIG. 3A is an overall view of a first alternate embodiment for a colorimetric indicator for breath, air, gas and vapor analyses, wherein one conduit indicates volume of breath and another conduit indicates the presence of an analyte such as alcohol, before reaction with exhaled breath.
Figure 3B:
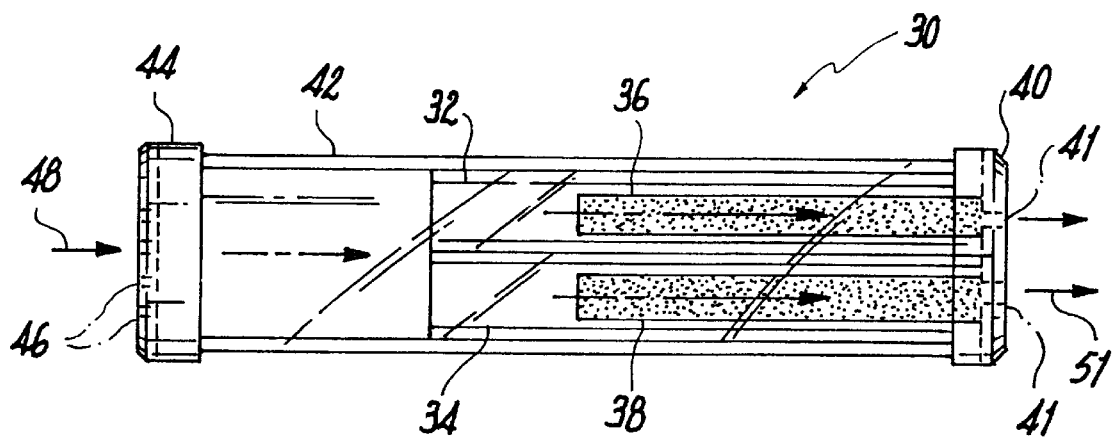
FIG. 3B is an overall view of the colorimetric indicator for breath, air, gas and vapor analyses as in FIG. 3A, wherein one conduit indicates volume of breath and another conduit indicates the presence of an analyte such as alcohol, after reaction with exhaled breath.
Figure 3C:
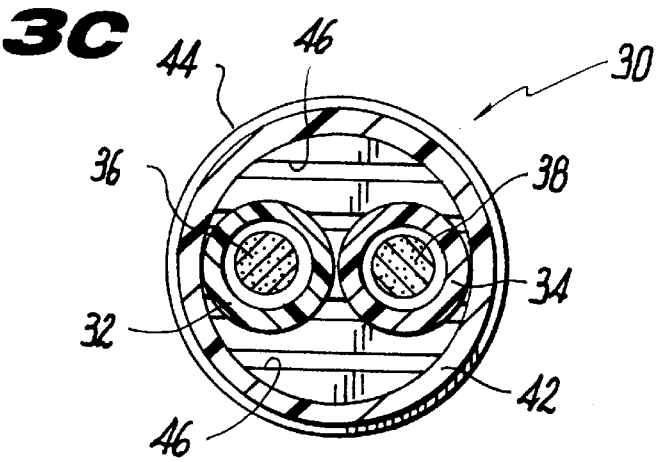

An alternate embodiment of a colorimetric indicator for breath, air, gas, & vapor analyses 30 shown in FIGS. 3A, 3B, and 3C is substantially the same as the colorimetric indicator for breath, air, gas, & vapor analyses 2 shown in FIGS. 1 and 2, except that two substantially parallel hollow inner tubes 32 and 34 are used to house breath volume indicator 36 and analyte indicator reagent 38, within each of the inner tubes 32 and 34, respectively. The two substantially parallel hollow inner tubes 32 and 34 containing, the breath volume indicator 36 and the analyte indicator reagent 38 are each affixed to exit end cap 40 having exit ports 41, and inserted into hollow outer tube 42. The exit end cap 40 is then coaxially affixed to the hollow outer tube 42. An entrance cap 44 having entrance ports 46 is coaxially affixed to the hollow outer tube 42 at an opposing end to the hollow exit cap 40.

The breath volume indicator 36 and the analyte indicator reagent 38 have sufficient porosity such that exhaled breath 48 of a user is easily blown through and around the circumferential periphery of the breath volume indicators 36 and the analyte indicator reagent 38 without undue strain on the part of the user.

The exhaled breath 48 enters the colorimetric indicator for breath, air, gas, & vapor analyses 30 through the entrance ports 46 and is passed through and around the circumferential periphery of the breath volume indicator 36 and the analyte indicator reagent 38 within the hollow inner tubes 32 and 34, respectively. The exhaled breath 48 is discharged from the colorimetric indicator for breath, air, gas, & vapor analyses 30 through the exit ports 41 along paths 51. When the breath volume indicator 36 turns a predetermined color, a fixed volume of gas has entered the colorimetric indicator for breath, air, gas, & vapor analyses 30, and the user stops blowing into the colorimetric indicator for breath, air, gas, & vapor analyses 30. When and if the chemical reagent within analyte indicator reagent 38 within the hollow inner tube 34 changes to another predetermined color, the presence of a level of a predetermined amount of an analyte, such as alcohol is indicated.

FIG. 3A shows the breath volume indicator 36 and the analyte indicator reagent 38 prior to the user blowing into the colorimetric indicator for breath, air, gas, & vapor analyses 30, each prior to turning to predetermined colors.

FIG. 3B shows the breath volume indicator 36 after the user breathes into the colorimetric indicator for breath, air, gas, & vapor analyses 30 and after the breath volume indicator 36 and the analyte indicator reagent 38 have each turned to predetermined colors.

The colorimetric indicator for breath, air, gas, & vapor analyses 30 may be constructed of transparent polyvinyl chloride material, glass, or other suitable material that allows the user to observe the breath volume indicator 36 and the analyte indicator reagent 38 each to change color.

FIGS. 4A and 4B show alternate rectangular 54 and cylindrical 56 form factors, respectively that may be used for both the breath volume indicator 36 or the analyte indicator reagent 38, within each of the inner tubes 32 and 34, respectively for the colorimetric indicator for breath, air, gas, & vapor analyses 30 shown in FIGS. 3A and 3B.

An alternate embodiment of a colorimetric indicator for breath, air, gas, & vapor analyses 60 shown in FIGS. 5A and 5B is substantially the same as the colorimetric indicator for breath, air, gas, & vapor analyses 30 shown in FIGS. 3A and 3B, except that a plurality of breath volume indicators 62A and 62B and a plurality of analyte indicator reagents 64A and 64B are housed within each of inner tubes 66 and 68, respectively. Each of the breath volume indicators 62A and 62B has different preset threshold levels and are used, for example, to indicate different preset volume thresholds, which may be required for indication of the concentration of different analytes in a user's exhaled breath 66, for example alcohol and cannabis. The analyte indicator reagents 64A and 64b may be of different reagents, each different reagent being used to indicate the presence of the different analytes, as already mentioned. In the case where several analytes must be indicated, then several breath volume indicators and several analyte indicator reagents may be incorporated into the colorimetric indicator for breath, air, gas, & vapor analyses 60. For example, there may be a need to indicate the concentration of alcohol, acetone, and cannabis in a diabetic user's breath. This could entail three breath volume indicators and three analyte indicator reagents, each having different reagents for the indication of the aforementioned substances. Such a device could be used by law enforcement agencies to confirm measurement of expensive computerized, which could give erroneous indications of alcohol for a diabetic, since acetone in the diabetic's breath may create interference during the measurement of alcohol in the diabetic user's breath.

The breath volume indicator 62A and 62B and the analyte indicator reagent 64A and 64B have sufficient porosity such that the exhaled breath 66 of a user is easily blown through and around the circumferential periphery of the breath volume indicators 62A and 62B and the analyte indicator reagents 64A and 64B without undue strain on the part of the user.

FIG. 5A shows the breath volume indicators 62A and 62B and the analyte indicator reagents 64A and 64B prior to the user blowing into the colorimetric indicator for breath, air, gas, & vapor analyses 60, each prior to changing to predetermined colors.

FIG. 5B shows the breath volume indicator 36 after the user breathes into the colorimetric indicator for breath, air, gas, & vapor analyses 60 and after the breath volume indicator 62A and 62B have each changed colors and only the analyte indicator reagent 64A having changed to a predetermined color. In this case the user has indicated positive for the presence of one analyte but not the other, for example, positive for alcohol and negative for cannabis.

An alternate embodiment of a colorimetric indicator for breath, air, gas, & vapor analyses 80 shown in FIGS. 6 and 6A is substantially the same as the colorimetric indicator for breath, air, gas, & vapor analyses 30 shown in FIGS. 3A, 3B, and 3C, except that cylindrical breath volume indicator 82 and cylindrical analyte indicator reagent 84 are located collinearly within a single hollow outer tube 86.

An alternate embodiment of a colorimetric indicator for breath, air, gas, & vapor analyses 90 shown in FIGS. 7 and 7A is substantially the same as the colorimetric indicator for breath, air, gas, & vapor analyses 80 shown in FIGS. 6 and 6A, except that semicylindrical breath volume indicator 92 and semicylindrical analyte indicator reagent 94 are abutted together at planar surfaces 96 and located within a single hollow outer tube 98. The semicylindrical breath volume indicator 92 and the semicylindrical analyte indicator reagent 94 may each be half cylinders or mating partial cylinders to form a full cylinder when abutted to one another.

Figure 8:
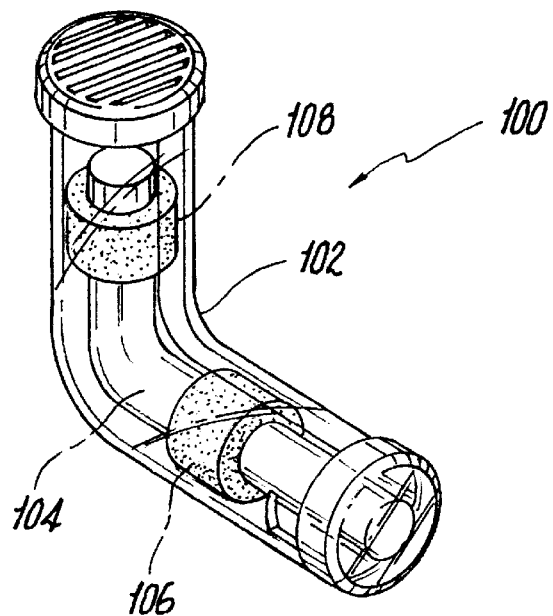
FIG. 8 is a perspective view of a seventh alternate embodiment for a colorimetric indicator for breath, air, gas and vapor analyses, wherein one J-shaped inner conduit is coaxially positioned within a further J-shaped outer conduit.

An alternate embodiment of a colorimetric indicator for breath, air, gas, & vapor analyses 100 shown in FIGS. 8 is substantially the same as the colorimetric indicator for breath, air, gas, & vapor analyses 2 shown in FIGS. 1 and 2, except that outer tube 102 and inner tube 304 are formed in a substantially "L" shape, the hollow inner tube 104 being coaxially located within the outer tube 102, and having breath volume indicator 106 and analyte indicator reagent 108 located coaxially between the inner tube 104 and the outer tube 102.

Figure 9:
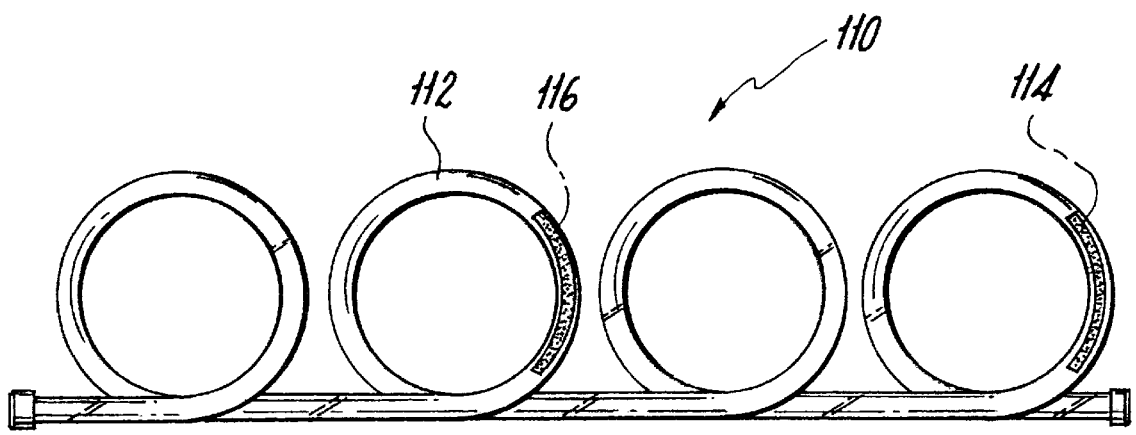
FIG. 9 is a side elevation view of an eighth alternate embodiment for a colorimetric indicator for breath, air, gas and vapor analyses; wherein a conduit is looped.

An alternate embodiment of a colorimetric indicator for breath, air, gas, & vapor analyses 110 shown in FIGS. 9 is substantially the same as the colorimetric indicator for breath, air, gas, & vapor analyses 80 shown in FIGS. 6 and 6A, except that tube 112 is formed in a plurality of loops and houses breath volume indicator 114 and analyte indicator reagent 116, each having rectangular form factors, as in FIG. 4A.

FIG. 10 is a plot of volume of exhaled air versus transition zone. The volume-measuring device employed consists of nine pads of blue reagent that turn pink when exposed to air. The location labeled "transition zone" is determined by the two adjacent pads whereby one is pink and the next pad is blue. Thus, this plot demonstrates that multi-segmented strip can be employed to determine more than one volume set point.

FIG. 11 is a plot of volume of exhaled air versus length of indicator. The data of this plot are obtained by assembling various volume-measuring devices where by each have a successively longer strip of a singles blue reagent. The volume of exhaled air necessary to turn the entire length of strip pink is recorded on the ordinate. This plot demonstrates that a single volume set-point can be created by adjusting the length of reagent strip.

It is known that other modifications may be made to the present invention, without departing from the scope of the invention.

For example, the device may be a hollow housing of a configuration other than a tube, such as a housing having a square or triangular cross section. Moreover, the outlet part may be either axially aligned with the inlet mouthpiece, or it may extend outwards from the housing in a different direction, such as perpendicular to the axis of the housing. The housing is not limited to Cartesian style shapes: circular, spiral, or "J" type housings may be appropriate depending on the specific application. Moreover, the housing is preferably transparent, so that the breath volume indicator and the analyte indicating reagent (i.e., alcohol) may be viewed for their respective colorimetric quantities. However, the housing could also be opaque, if the colorimetric readings are read by an optical detector within the housing, and then displayed digitally or by analog on a measuring gauge exterior to the housing.

A user desiring to determine physiological status or condition based on a colorimetric measurement of exhaled breath would use this device as follows. The colorimetric indicator for breath, air, gas, and vapor analyses may be stored in an air-tight container or wrapping, such as cellophane or mylar-coated plastic prior to use, so as not to contaminate the volume indicator element or the reagent analyte. Upon removal of the colorimetric indicator for breath, air, gas, and vapor analyses from the air-tight container, the user exhales through the mouthpiece end of the device until the volume indicator region completes a color change, for example a zone or zones on the device changes from blue to pink. This color change could result from one to three or four breaths and contain 2 liters of exhaled breath. At the same time, a different zone or zones on the device may be changing color as well. For example, if this analyte region changes from yellow to green then the user is warned that they may be legally intoxicated, i.e., a "positive" indication for a preset level of analyte. If no color change is viewed in this other zone or zones, then the device shows a "negative" indication for a preset level of analyte. The user would simply dispose the device, and in time retest if desired with a fresh unit. The volume of sample breath and level of alcohol necessary to induce a color change have all been previously determined and set during the manufacturing process.

OPERATION OF A VOLUME INDICATING ELEMENT

By immobilizing a reagent on a strip or powder support and contacting the immobilized reagent on the strip or powder support with an analyte mixture composed of at least one constant concentration component, a device can be created that is capable of indicating a volume of breath, air, gas, or vapor that has passed the vicinity of the strip or powder support, without the need to measure the flow rate or duration of flow, directly. Such a device acts as a chemical accumulator. The immobilized reagent reacts directly with the constant concentration component. This reagent is called the volume indicator reagent since its function is to indicate a volume of breath, vapor, gas, or air has been in contact with the reagent. The total number of moles of a component passing through the device are measured, and may be described by the relationship in Equation 1:

$$M_1 = C_1 * F * T \qquad \text{Equation 1}$$

where: $M_1$=moles of constant concentration component, $C_1$=concentration of one component introduced to the device, is constant, and typically moles/liter, F=flow rate of sample introduction, in liters/minute, and T=time or duration of sample introduction, in minutes.

A fixed number of moles (M) passing through the device is accomplished by immobilizing a fixed number of moles of reagent on a strip or powder support. Once the reagent is consumed, a fixed number of moles of constant concentration component have passed through the device. For the case of a strip, the total number of moles of reagent available is then proportional to the length of the strip. Similarly, for a powder, the total number of moles is proportional to the quantity of powder support employed. Likewise, for beads or spheres, the total number of moles is proportional to the quantity of reagent employed on the beads or spheres. One can conclude from Equation 1 that to indicate a certain quantity of moles M, a multitude of flow rates (F) and times (T) will satisfy the conditions of Equation 1. Thus, as an accumulator, the end point of complete consumption of reagent is reached independently of flow rate and time.

Consider at the same time subjecting the device to a mixture containing a second component, whereas with this other component one desires to know whether a certain threshold level has been attained or exceeded. This second component could be present at various levels depending on the environment containing the second component. The number of moles of the second component introduced to the device is described by Equation 2:

$$M_2 = C_2 * F * T \qquad \text{Equation 2}$$

where: $M_2$ = moles of second component, $C_2$ = concentration of second component introduced to device, is dependent on environment, and typically moles/liter, F = flow rate of sample introduction, in liters/minute, and T = time or duration of sample introduction, in minutes.

Now, in both Equation 1 and Equation 2 the flow rates F and duration of flow T are the same, since both components are being introduced at the same time. One component $C_1$ is fixed for all sampled environments, whereas the other component $C_2$ is variable and is desired to be known. Similar to $C_1$, a reagent specific to $C_2$ is immobilized on a planar, granular, or spherical solid support located within the same device as mentioned above. Since by adjusting the amount of reagent for $C_1$, one can indicate to the user to halt introducing sample at a fixed point ($M_1$ reagent totally reacted); the number of moles of $M_1$ accumulated actually relates to a fixed volume of sample introduced (F*T). Thus, one guarantees that the same fixed volume is being used for determining a level of $M_2$ and subsequently $C_2$, or the concentration of the second component can then be known. This reagent that reacts with $M_2$ is the analyte indicator reagent and is selected based on the material one desires to monitor. Examples of relevant analytes for the health, environmental, and industrial monitoring are methanol, ethanol, iso-propylalcohol, ethers, xylene, toluene, mineral spirits, turpentine, acetone, cannabis, hydrogen sulfide, carbon monoxide, nitrous oxides, or sulfur oxides. In practice, the specific quantities and concentrations of reagents for $C_1$ and $C_2$ as well as the lengths of solid supports would all be determined in a manner similar to that described in the experimental examples. Typically, one strives to immobilize as great an amount of reagent (either analyte or volume indicting) on the support. The quantity of reagent-immobilized support used for the device, whether that be mass of granular support or length and width of planar support is defined by 1) the desired volume of breath sample, and 2) the concentration or concentrations of analyte one desires to indicate. For example, the state of being legally intoxicated. Once the optimum dimensions and reagent concentrations has been determined for a specific analyte, then the device is manufactured to meet those specifications.

Certain conditions must be met in order for this device to function. First, one component of the analysis mixture must be constant concentration. While this may appear to be a constraint requirement, there are a surprising amount of situations whereby this condition can be met. For example, in sampling human or animal breath, air exhaled from the lungs is completely saturated with water. The water concentration is constant, so a reagent reacting with water would be appropriate. Similarly, in monitoring ambient environments, such as air quality in factories, hospitals, public spaces, etc., the concentration of oxygen is constant at 20.5% and could be used as the indicator "$M_1$".

Secondly, one must select a reagent that completely reacts with this "constant" component $M_1$. Either the reaction is irreversibly complete, or for the reversible case the equilibrium state is readily attained for the reaction with the component, but the reverse reaction (loss of component) occurs much more slowly. Examples of two equilibrium cases follow.

Transition metal complexes are compounds composed of one or more metals (M) bound up by one or more ligands (L). Often ligands can be exchanged such as depicted in Equation 3:

$$ML_x + yL^* \iff ML^*_y + xL \qquad \text{Equation 3}$$

Here, ligand "L" is being displaced by ligand "L*". Often these two states can be observed by a color change or a change in some other physical property. For example, Equation 4 shows a common reaction:

$$[CoCl_4]^{2-} + 6H_2O \iff [Co(H_2O)_6]^{2+} + 4Cl^- \qquad \text{Equation 4}$$

In this example, cobalt chloride is one of the reagents immobilized on a planar support in order to create a reagent for water. Cobalt chloride complex (blue) turns pink in the presence of water. Water in breath is used in this application as "$M_1$". The stoichiometry of Equation 4 also shows that for each mole of cobalt chloride, six moles of water are reacted. The actual stoichiometry of these ligand exchange reactions is not important to the functioning of the device. Incidentally, the structure of the chloride complex is tetrahedral, while the hydrated complex is octahedral. In this case, the color change is due to both the different ligands and the change in structure about the cobalt.

In another example, not all of the ligands about the complex are exchanged. Equation 5 describes this state:

$$ML_x + yL^* \iff ML^*_y L_{x-y} + yL \qquad \text{Equation 5}$$

where y<x, "L" is one type of ligand, and "L*" is a different ligand.

An example of this would be an oxygen-binding reaction, such as that outlined in Equation 6:

$$ML_x + O_2 \iff ML_{x-1}O_2 + L \qquad \text{Equation 6}$$

Here, one molecule of dioxygen binds the complex displacing one ligand "L". Reactions such as that in Equation 6 have been thoroughly studied as a result of efforts to synthesize artificial hemoglobin. Various applications employing these compounds are described in the literature, and one such application (U.S. Pat. No. 5,096,724) outlines ligands from the group of compounds polyalkylpolyamines, macrocylic compounds, and amino acids. All of these complexes change from a light red or pink color to brown, once oxygen is bound and would be suitable for the previous example of using oxygen as "$M_1$".

While the transition metal complexes represent a particularly potent group of reagents, other appropriate reagents are available based on organic, organometallic, or inorganic compounds; or mixtures of two or more of all these classes.

Although the above examples describe a visible color change, a third condition for the device is more general, that is at least one state of the indicator for "$M_1$" must be measurable, whether that be visual with the human eye (for example, see a strip completely change from blue to pink), or through appropriate instrumentation, such as spectrophotometers (UV-VIS-IR), or electrochemical (conductivity, potentiometry, or amperometric means).

The configuration of assembling the planar, granular, or spherical support will not effect the chemistry or function of the volume indicating device. Instead, configurations of convenience and ease-of-use are desired, and these may take a variety of shapes and forms. For example, if one desires to sample 2L of exhaled air, one can use a single strip of appropriate length (see experimental examples) and inform the user to continue blowing until the strip's color is completely changed. As an alternative, one could calibrate a strip-containing tube with hash-marks, and once the color change has crossed a mark, the user stops breathing through the strip-containing tube, and a finite volume has been sampled. Finally, as a last example, one could consider three zones in a tube. Zone one and zone three are volume-measuring indicators, while zone two is an indicator for the analyte of interest. The user would be instructed to continue passing a breath sample through the tube (via breathing or a gas pump), until the new color in zone one matches zone three.

Furthermore, these zones are not restricted to symmetrical or equal sizes. A series of segmented strips could be constructed, whereupon each strip is composed of ever-increasing length. Such an arrangement would impart to the user a visual indication beyond color change for greater amounts of breath volume or analyte. Similarly, a granular form can be constructed by employing a sequence of ever increasing grain or bead size, with the largest elements indicating the greatest amount of volume or analyte.

IMMOBILIZATION OF BOTH VOLUME—INDICATING REAGENT AMD MONITORED SUBSTANCE REAGENT

A. Planar Immobilization of a reagent previously bound to a granular support.

Granular supports are often used as a solid means to hold or trap a reagent. For example, silica is used in many examples of ethanol-indicating reagents, such as dichromate. Although a tube filled with silica granules can perform the analysis, it is often desired and preferred to used planar supports. Planar supports are more easily incorporated into simple devices; special means to trap the silica are not necessary. "Dead zones" of uneven gas flow are not usually encountered with planar supports. Manufacturing is easier, as well as less expensive, since costly handling steps are avoided. Finally, accidental access by the user is avoided; a broken device would not leak silica if the granular support were immobilized in planar form.

There are several methods to immobilize planar supports, such as silica, ion-exchange beads, and polystyrene beads, for example. In the present invention, a method is disclosed, whereby an adhesive is coated on an inert planar support such as polystyrene, Teflon, or Styrofoam. The granular support is pressed into the adhesive, and excess grains are removed.

Another approach is to create a heterogeneous phase consisting of an inert polymer melt or solution and the granular support. The polymer support is then cast as a film and cooled (or subject to solvent evaporation). Inert polymer films include but are not limited to: polypropylene, polyethylene, polystyrene, polyvinylidene fluoride, etc.

B. Immobilization directly on a planar support.

For some reagents, it is preferred to directly immobilize the reagent on a planar support, film, or membrane. For some cases, the consistency and ease of handling afforded by a homogeneous polymeric film with integral immobilized reagent is preferred.

A charged polymeric support, for example, can be a good substrate for reagents of opposite charge. Potassium dichromate, often used as a reagent for ethanol, is a dianion. Thus, one would prefer to use a positively charged membrane to bind the dichromate. Some examples of commercially available membranes that meet this criteria are: Tokyoma Soda's Tosflex, composed of a perfluorinated polymer support modified to contain quaternized amine groups, Neosepta's non-perfluorinated polymer supports modified to contain quaternized amine groups, and RAI's Raipore polytetrafluoroethylene support with radiation-grafted ion exchange groups. One would simply mix a solution of the reagent and add a sheet of the membrane to the solution, dry, and cut into the appropriate length strip to insert in the device.

For a cationic reagent, such as the oxygen binding compounds mentioned as the volume-indicating reagent, where oxygen is the constant-concentration component, negatively charged membranes would be desired. These are also commercially available. For example, DuPont provides Nafion®, consisting of a perfluorinated polymer support with sulfonic acid groups covalently attached to the support. Neosepta's non-perfluorinated polymer supports have also been modified to contain sulfonic acid groups, as have RAI's Raipore polytetrafluoroethylene support with radiation-grafted ion groups. A procedure similar to that mentioned above would immobilize the catonic reagent.

In the case where an uncharged polymer support is desired, such as polyvinylalcohol, ion-pair reagents can be used. For example, large anions such as telrafluroborate could bind and neutralize cationic reagents. Similarly, the quaternary amines such as tetraethylammonium chloride could be used with anionic reagents. In both cases, the complex will extract into a non-polar or slightly polar medium such as polyvinylalcohol and be available for a reaction.

However, as previously described in earlier examples, non-specific absorption can be employed as well. Simple cellulose or glass fiber filter papers can be employed to bind reagents based on small differences in charge, hydrophillic, or hydrophobic interactions.

IMMOBILIZATION STRATEGIES AND PARTICULARS ON VOLUME-INDICATING ELEMENTS WITH EXAMPLES

A. Factors Controlling the Magnitude of Volume Measured i. Concentration of Reagent Since the volume-indicating reagent acts as a measure of the extent of reaction between the constant concentration component and the volume-indicating reagent, it is obvious that once the reagent has completely reacted, no further color change is possible, and no further volume indication occurs. Similarly, if a planar support or strip of filter paper of fixed dimensions is treated with increasingly more concentrated solutions of volume-indicating reagent, a larger volume cut-off could be possible. One would expect the relationship between indicator concentration and volume capacity to be linear: a doubling of indicator concentration used to make the strip would allow a doubling of measured volume. This relationship will not hold when a very concentrated form of reagent is employed. At the very high concentration, not all of the reagent will be accessible for complete reaction. Similarly, nuances of the tube construction may affect the portionality constant. Thus, in order to adjust the cut-off point for the volume of breath one would like to indicate, one could adjust the amount of reagent immobilized by varying the initial concentration of reagent added to the support mix.

ii. Sensitivity of Reagent

In addition to adjusting the concentration of the reagent, one can change the inherent sensitivity of a reagent's reaction with the constant concentration component. This de-sensitization is accomplished by adding a compound that competes with the reagent or modifies the reagent. For example, if the constant-concentration component is water, one could employ $CoCl_4$ as the reagent that changes from blue to pink upon exposure to water. However, unmodified forms of this reagent may be too sensitive to water, and thus could react with all water presented to the reagent. Thus, one could add hydroxide ($OH^-$) to compete with the chloride binding the cobalt (see Equation 7):

$$[CoCl_4]^{2-} + 4OH^- \rightleftarrows [Co(OH)_4]^{2-} + 4Cl^- \qquad \text{Equation 7}$$

If one were to add less than a stoichiometric quantity of $OH^-$, one would obtain a mixture of cobalt chloride, cobalt hydroxide, and a complex containing both chloride and hydroxide bound to the cobalt. The amount of OH⁻ added will change the overall equilibrium point between the chloride form and its reaction with water (see Equation 8 below for an intermediate state). Since these are now complex equilibrium with non-unit stoichiometry, the change in volume sensitivity is no longer directly or simply proportional to the concentration of OH⁻ added (that is, a doubling of OH added does not lead to a halving of volume sensitivity).

Equation 8

A paper strip containing this mixture and having a lowered sensitivity to water is made as follows. Prepare a 1M solution of cobalt (II) chloride by mixing 23.8 grams of the cobalt complex with 100 mL of water. Slowly add 50 mL of a 1M KOH solution to the cobalt solution. After stirring dip filter paper (a strip 2*0.5 cm of cotton cellulose) until completely saturated with reagent, place the paper in a vacuum oven at moderate temperature and vacuum until dry. Store in a closed container.

If this strip were compared to a strip made with only 1M cobalt (II) chloride the hydroxide form would need an excess of water to react with the reagent and thus have both a reduced sensitivity and an increased capacity to measure or indicate volume set points.

The principle outlined above details one method to reduce the sensitivity of a transition metal complex reagent to the analyte of interest. That is, by adjusting the kind and nature of ligands complexing the metal center, different affinities for the analyte are induced. These various affinities ultimately change the reaction ratio between analyte and reagent, and thus control the number of moles (M) accumulated in the reactive zone. For example, if one desires to create a series of zones that indicate ever greater breath volumes, one could use this desensitizing principle.

One is not limited to the use of one reagent for each zone. For example, a series of volume indicating reagents from the group comprising transition metal complexes, organic, inorganic, or organometallic compounds could be selected such that one tailors a multitude of reactive zones with different capabilities to accumulate and react with different molar(M) levels of the constant concentration component.

An example of using the densitizing principle for transition metal complexes to create multiple zones on one strip follows.

Example 1: A series of nine cotton cellulose strips are constructed so that eight of the cotton strips contain a mixture of cobalt chloride and cobalt hydroxide, while one of the cotton strips is completely cobalt chloride without the hydroxide form. These strips are arranged as discrete areas as shown by the sketch at the bottom of FIG. 10. The nine strips are numbered 1–9 whereby strip 1 is composed only of cobalt chloride, while strips 2–9 have an increasingly greater proportion of hydroxide added to the mix. This strip that is approximately 8*1 cm is inserted into a tube (1.1 cm. dia, 9 cm. long). As air is exhaled into the tube, the zone of water-saturated air moves along the strip. For this example, the actual volume of air passing through the tube is verified by collecting the exiting vapors via an inverted water-filled graduated cylinder. The greater the volume of breath that a user breaths into the tube, the further down the tube the transition of blue to pink moves. FIG. 10 is a plot of the transition zone versus the volume of air expelled into the tube. Each transition zone is defined by referring again to the sketch at the bottom of FIG. 10.

This example illustrates the use of a volume indicating reagent that reacts with water, a constant component in exhaled air. This water is refereed to as "$M_1$" in the theory section. By creating different zones each possessing a different affinity for water, more than one set point for breath volume could be indicated with this device.

Such a design is not limited to just one varying mixture of volume-indicating reagent. For example, each zone 1–9 could be composed of a different reagent that reacts with the constant-concentration component in accordance with the reagent's specific chemistry, and, for example, yields a different color and reacts with different sensitivities. These volume indicating reagents could be selected from the group comprising transition metal complexes, organic, inorganic, or organometallic compounds, or mixtures of two or more. In this way one could use a color coding to indicate a particular level of volume that has been attained.

iii. Length of Support

By far the simplest method to adjust the volume set point is to change the dimensions of the volume-indicating strip. Since the volume-indicating reagent acts as an accumulator, if follows that by changing the length of the volume-indicating strip one can adjust the quantity of accumulator present. Thus, if one were to prepare a strip containing a fixed quantity of volume-indicating reagent, and then cut the strip in half, the volume set point would be expected to be reduced by approximately half. Similarly, if one employed granular or bead supports, one could reduce or increase the mass of granular of bead support employed to vary the volume set point.

This principle is illustrated for a planar strip support in the example below.

Example 2: A filter paper strip is prepared in a manner similar to that described in Example 1, by soaking a cotton cellulose paper strip 4 cm long by 1 cm in approximately 2M cobalt (II) chloride and drying overnight in a vacuum oven. The strip is inserted into a tube (1.1 cm. dia, 9 cm. long). As air is exhaled into the tube, the zone of water-saturated air moves along the strip. Measurements of actual volume are verified using the cylinder apparatus of Example 1. The more volume a user breaths into the tube, the further down the tube the transition of blue to pink moves. The actual section on the strip that shows where the reagent has been reacted is indicated as a length on the graph, as shown in FIG. 11. This example contrasts to the previous in that the volume indicating device of Example 1 is composed of discrete zones each containing a different affinity for the constant component substance water. In this example we employ a continuous strip with the same reagent homogeneously dispersed throughout. In practice, one could either indicate a threshold point with a line etched in the tube, or use a length of volume-indicating strip that matches the desired volume set point; once the entire strip has changed color, the volume set-point is reached, and the user would halt exhaling into the tube.

This example demonstrates that the length of a strip of support containing the volume-indicating reagent can be varied to achieve various amounts of "$M_1$", which in turn limits the number of moles of constant concentration component that can be accumulated, and thus indicate a fixed volume of breath exhaled into the device.

Although the device is not intended to be limited by indicating only water as the constant-concentration component, or cobalt chloride as the volume-indicating reagent, similar strips have been employed to indicate relative humidity in the home, for food, or for objects that are water sensitive like electronic components. Companies such as Humidor Co., (Coulter, Calif.). Multiform Dessicants (Buffalo, N.Y.), or Fisher Scientific Company (Springfield, N.Y.) all make humidity-indicating strips that could also be employed in this device.

It is a further advantage of such systems to employ indicating humidity papers that change color at the lower relative humidity range between 5–10 %RH. Thus, if a package has been accidentally opened or used, the pink indicator will be pink and warn that the device is in a "used" state.

In some applications one desires a volume element that instantly renders one of many possible volume states. For example, as previously discussed, a strip containing different areas of various volume-indicating reagents with each possessing a different sensitivity to the volume-indicating reactant can be constructed in a similar manor, one can create the same effect by immobilizing appropriate volume-indicating reagents on solid supports. These supports could be granular or round silica, beads containing an absorptive capacity (for example methyl cellulose), beads chemically modified to specifically bind the reagent (for example, modified nylon, polystyrene, or polyacrylamide beads. Thus, various zones containing beads or solid or porous non-planar supports could be distributed within a container or within a zone formed by two (concentric containers. Each zone is characterized by containing a different form or strength of the volume-containing reagent. Thus, when used in a device, one of many possible volume states may be indicated The following example is an illustration for the construction of a volume indicating reagent on a granular support.

Example 3: Granular Breath Volume Indicator

This example demonstrates the use of a particulate form of cobalt chloride immobilized on silica. "Indicating Drierite" (Fisher Scientific, Pittsburgh, PA.) 6–10 mesh is ground with a mortar and pestle to between 20 and 200 mesh. A tube (1.1 cm in diameter, 9 cm long) is outfitted with an interior tube (0.7 cm. in diameter, 9 cm long) whereby approximately 1 mm interstitial space is formed between the two. A layer of ground drierite is inserted between the two tubes by coating the inner tube with an adhesive tape (3M,) and sticking approximately 0.2 gm of the ground indicator to the inner tube. The coated inner tube is inserted into the larger tube. As in the previous examples, the exit of this tube assembly is connected to a flexible tube and a graduated cylinder is filled with water and placed in an inverted orientation in a vessel of water. As air is passed through the tubes, the exhaled air is collected in the cylinder and the total exhaled breath volume measured. The indicator changes from blue to pink denoting a volume of water vapor from the exhaled breath has passed. The extent of the color change along the tube is a function of the moles of constant component substance, water ($M_1$) and thus the air volume passed though the tube. In this example, breaths totaling 0.5 L enabled a discernible and complete color change. This example shows that a color change can be fixed to a volume of breath using immobilized reagents on granular supports.

IMMOBILIZATION OF MONITORED SUBSTANCE REAGENT(S)

Just as the previous examples discussed generalized methods to immobilize the volume indicator reagent ($M_1$), the same or similar methods can be employed to immobilize the analyte indicator reagent ($M_2$). An example for visually indicating alcohol in breath follows. Such a system, or similar embodiments could be readily mated to the volume indicator element to form a complete system for determining alcohol in the breath or other desired substances.

Example 4: Granular Indicator for Alcohol

Prepare granular solid support by mixing 27 grams of 70–230 mesh silica gel (American Scientific Products, IL) with 200 mL D/I water, and 40 mL concentrated nitric acid. Stir at room temperature overnight. Filter, rinse with D/I water, and vacuum dry. Prepare a 0.2 L of a solution of 1M potassium dichromate ($K_2Cr_2O_7$) in 1M sulfuric acid ($H_2SO_4$). Mix pretreated support with the potassium dichromate/acid solution overnight. Filter, rinse extensively. Dry in vacuum oven at 40° C. for 4 hours.

Pack granular support into the interstitial space of a tube assembly, or immobilize onto a strip comprised of an inert plastic film and an adhesive. For the case of a strip (5×0.7 cm) approximately 0.1 grams of indicator is immobilized, as measured via an electronic balance. Insert the strip inside the middle of a testing tube 10 cm long by 1 cm diameter.

Various levels of alcohol vapor are readily introduced into the device by mixing fixed amounts of ethanol with water, rinsing and gargling for at least 5 minutes, and exhaling into a tube connected to the volume-measuring device described previously. The results of tests obtained using this indicator are summarized in Table 1 below.

TABLE 1

Tests on six individual tubes containing alcohol reagent of Example 4

| Test No.) alcohol level in mix | Volume passed | Results |
|---|---|---|
| 1) Ethanol - 1% | 1.5 L | no color change |
| 2) Ethanol - 5% | 1.5 L | no color change |
| 3) Ethanol - 7% | 1.5 L | color changes from yellow to green |
| 4) Ethanol - 12% | 1.5 L | color changes from yellow to green |
| 5) Control - 0% | 1.5 L | no color change |
| 6) Control - 0%, followed by 12% in ethanol mix | 1.5 L, 1.5 L | no color change, no color change |

The results of Table 1 demonstrate the device will 1) change color only upon exposure to ethanol, 2) will change at a prescribed level of ethanol (that is, not at 5% base mix while indicting at 7%), and 3) as seen in the results of experiment (6), will only work as a single-use device. This example also demonstrates that a color change can be fixed to a volume of breath containing alcohol using immobilized indicating reagents on support strips.

Different embodiments of the present invention and method of manufacture may be used for colorimetric indicators for breath, air, gas, & vapor analyses and method of manufacture.

Although the present invention has been described in considerable detail with reference to certain preferred versions thereof, other versions are possible. Therefore, the spirit and scope of the appended claims should not be limited to the description of the preferred versions contained herein.

What is claimed is:

1. A colorimetric indicator for breath, air, gas, and vapor analyses, comprising:

a housing having at least one inlet for passage of said breath, air, gas, and vapor into said housing and at least one outlet for passage of said breath, air, gas, and vapor out of said housing;

a first chemical reactant within said housing in contact with said breath, air, gas, and vapor passing therethrough for indicating directly when a fixed volumetric quantity of said breath, air, gas, and vapor has passed through said housing; and a second chemical reactant within said housing in contact with said breath, air, gas, and vapor passing therethrough for indicating directly whether a predetermined threshold amount of a predetermined analyte has been reached during passage of said fixed volumetric quantity of breath, air, gas, and vapor.

2. The colorimetric indicator for breath, air, gas, and vapor analyses according to claim 1 wherein said chemical reactant is selected from the group consisting of transition metal complexes, organometallic compounds, inorganic compounds and organic compounds.

3. The colorimetric indicator for breath, air, gas, and vapor analyses according to claim 1 wherein said chemical reactant is selected from the group consisting of cobalt chloride, cobalt hydroxide, compounds of cobalt and polyalkylpolyamine ligands, compounds of cobalt and macrocyclic ligands, compounds of cobalt and amino acid ligands, and compounds of cobalt and salen type ligands.

4. The colorimetric indicator for breath, air, gas, and vapor analyses according to claim 1 wherein said chemical reactant for indicating volume is selected from the group consisting of compounds of iron and polyalkylpolyamine ligands, compounds of iron and macrocyclic ligands, compounds of iron and amino acid ligands, compounds of iron and salen type ligands, compounds of nickel and polyalkylpolyamine ligands, compounds of nickel and macrocyclic ligands, compounds of nickel and amino acid ligands, compounds of nickel and salen types ligands, compounds of copper and polyalkylpolyamine ligands, compounds of copper and macrocyclic ligand, compounds of copper and amino acid ligands; compounds of copper and salen type ligands, compounds of zinc and polyalkylpolyamine ligands, compounds of zinc and macrocyclic ligands, compounds of zinc and amino acid ligands, and compounds of zinc and salen type ligands.

5. The colorimetric indicator for breath, air, gas, and vapor analyses according to claim 1 wherein said first chemical reactant for indicating volume, is selected from the group consisting of Vitamin B12, phthalocyanines, and pyterines, porphyrins.

6. The colorimetric indicator for breath, air, gas, and vapor analyses according to claim 1 wherein said first chemical reactant for indicating volume, is selected from the group consisting of iron, copper, nickel, silver.

7. The colorimetric indicator for breath, air, gas, and vapor analyses according to claim 1 wherein said first chemical reactant for indicating volume, is selected from the group consisting of redox dyes and pH indicators.

8. The colorimetric indicator for breath, air, gas, and vapor analyses according to claim 7 wherein said chemical reactant for indicating volume is selected from the group consisting of Vitamin B12, phthalocyanines, pyterines, and porphyrins.

9. The colorimetric indicator for breath, air, gas, and vapor analyses according to claim 1 wherein said said second chemical reactant is selected from the group consisting of chromates, dichromates, permanganates, silver ions and alcohol dehydrogenases.

10. The colorimetric indicator as in claim 1 wherein said housing comprises at least one conduit, wherein said entrance port is an open breathing mouthpiece at one end and further wherein said exit port is an open output port at another end.

11. The colorimetric indicator as in claim 10 wherein said chemical reactant for indicating presence of a chemical concentration of analyte is located within said at least one conduit.

12. The colorimetric indicator as in claim 10 wherein said chemical reactant for indicating a volume of breath is located within said at least one conduit.

13. The colorimetric indicator as in claim 10 further comprising a user-openable discardable air-tight container enclosing said at least one conduit.

14. The colorimetric indicator as in claim 13 wherein said user-openable discardable air-tight container comprises cellophane.

15. The colorimetric indicator as in claim 13 wherein said user-openable discardable air-tight container comprises mylar-coated plastic.

16. The colorimetric indicator as in claim 1 wherein said first chemical reactant is in one predetermined zone which undergoes a change of color from one color to a different color and wherein said second chemical reactant is in another zone which undergoes a change of color from one predetermined color to a second predetermined color.

17. The colorimetric indicator as in claim 16 wherein said change of color of said second chemical reactant for indicating presence of said analyte indicates whether the user's breath alcohol level exceeds a predetermined threshold level of alcohol.

18. The colorimetric indicator as in claim 10 wherein said at least one conduit comprises a plurality of conduits, wherein one conduit includes a predetermined volume of breath and another conduit indicates the presence of said analyte.

19. The colorimetric indicator as in claim 18 wherein each said conduit includes a plurality of segments, each said segment indicating the presence of various concentrations of analyte within conduit.

20. The colorimetric indicator as in claim 18 wherein said at least one conduit includes a plurality of predetermined visually ascertainable zones, wherein one zone of said plurality of zones indicates breath volume and another zone of said plurality of zones indicates the presence of said analyte.

21. The colorimetric indicator as in claim 20 wherein said zones are parallel to each other.

22. The colorimetric indicator as in claim 20 wherein said plurality of conduits includes a pair of coaxial components, including an outer conduit enclosing an inner conduit.

23. The colorimetric indicator as in claim 10 wherein said mouthpiece includes a plurality of pores transversally engageable with exhaled breath of the user.

24. The colorimetric indicator as in claim 10 further comprising an interstitial space through which said interstitial space the exhaled air of the user contacts said.

25. The colorimetric indicator as in claim 10 wherein said housing is rectangular.

26. The colorimetric indicator as in claim 10 wherein said housing is cylindrical.

27. The colorimetric indicator as in claim 10 wherein said at least one conduit is tubular.

28. The colorimetric indicator as in claim 10 wherein said at least one conduit is square in cross section.

29. The colorimetric indicator as in claim 10 wherein said at least one conduit is triangular in cross section.

30. The colorimetric indicator as in claim 10 wherein said output port is axially aligned with said the inlet mouthpiece.

31. The colorimetric indicator as in claim 10 wherein said output port extends outward at an angle from said at least one conduit and said mouthpiece.

32. The colorimetric indicator as in claim 10 wherein said output port extends outward perpendicular to said at least one conduit and said mouthpiece.

33. The colorimetric indicator as in claim 10 wherein said at least one conduit extends linearly.

34. The colorimetric indicator as in claim 10 wherein said at least one conduit is circular in shape.

35. The colorimetric indicator as in claim 10 wherein said at least one conduit is spiral in shape.

36. The colorimetric indicator as in claim 10 wherein said at least one conduit is a "J" shape.

37. The colorimetric indicator as in claim 10 wherein said at least one conduit is transparent.

38. The colorimetric indicator as in claim 10 wherein said at least one conduit is opaque, and wherein said at least one conduit includes an optical detector within said at least one conduit, a display displaying the output of said optical detector.

39. The colorimetric indicator as in claim 38 wherein said display is digital.

40. The colorimetric indicator as in claim 38 wherein said display is analog.

41. The colorimetric indicator as in claim 10 further comprising a measuring gauge attached to an exterior of said at least one conduit.

42. The colorimetric indicator as in claim 10 wherein a portion of said at least one conduit is transparent.

* * * * *